United States Patent
Hamauzu

(10) Patent No.: US 11,972,559 B2
(45) Date of Patent: *Apr. 30, 2024

(54) RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Shin Hamauzu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

This patent is subject to a terminal disclaimer.

(21) Appl. No.: 17/157,023

(22) Filed: Jan. 25, 2021

(65) Prior Publication Data

US 2021/0251583 A1    Aug. 19, 2021

(30) Foreign Application Priority Data

Feb. 13, 2020  (JP) ................................ 2020-022641
Oct. 28, 2020  (JP) ................................ 2020-180637

(51) Int. Cl.
*G06T 7/00*    (2017.01)
*A61B 6/12*    (2006.01)
(Continued)

(52) U.S. Cl.
CPC .............. *G06T 7/0012* (2013.01); *A61B 6/12* (2013.01); *A61B 17/06066* (2013.01);
(Continued)

(58) Field of Classification Search
CPC ...... A61B 2034/2065; A61B 2090/376; A61B 34/20; A61N 2005/1062; G06F 18/2132; G06N 3/08; G16H 50/20; G06V 10/20; G06V 10/22; G06V 10/255; G06V 10/26; G06V 10/70; G06V 10/774; G06V 10/776;
(Continued)

(56) References Cited

U.S. PATENT DOCUMENTS 11,389,132 B2 *  7/2022  Hamauzu .............. A61B 6/5217
2006/0061595 A1 *  3/2006  Goede .................... G06F 16/51
                                                              707/E17.031
(Continued)

FOREIGN PATENT DOCUMENTS

JP   S52-056495 U    4/1977
JP   2012-235796 A   12/2012
(Continued)

OTHER PUBLICATIONS

Bmit (www.bmit.lightsource.ca/tech-info/techniques/#:~:text=The%20contrast%20is%20driven%20by,a%20high%20resolution%20composite%20image., retrieved Feb. 21, 2023).*
(Continued)

*Primary Examiner* — Carolyn A Pehlke
(74) *Attorney, Agent, or Firm* — Studebaker & Brackett PC

(57) ABSTRACT

A processor acquires a confirmation radiographic image including a surgical tool. In a case in which a radiographic image is input, the processor detects a region of the surgical tool from the confirmation radiographic image using a discriminator that detects the region of the surgical tool included in the radiographic image.

14 Claims, 7 Drawing Sheets

(51) Int. Cl.
  *A61B 17/06* (2006.01)
  *A61B 17/29* (2006.01)
  *A61B 17/3201* (2006.01)
  *A61B 17/3211* (2006.01)
  *A61F 2/07* (2013.01)
  *A61F 13/44* (2006.01)
  *G06T 7/11* (2017.01)
  *G06V 10/25* (2022.01)

(52) U.S. Cl.
  CPC .......... *A61B 17/29* (2013.01); *A61B 17/3201* (2013.01); *A61B 17/3211* (2013.01); *A61F 2/07* (2013.01); *A61F 13/44* (2013.01); *G06T 7/11* (2017.01); *G06V 10/25* (2022.01); *G06T 2207/10124* (2013.01); *G06T 2207/20081* (2013.01); *G06T 2207/30052* (2013.01)

(58) Field of Classification Search
  CPC . G06T 2207/20081; G06T 2207/20084; G06T 2207/30004; G06T 2207/30021; G06T 7/0012; G06T 7/0014; G06T 7/11; G06T 5/50; G06T 2207/20221
  See application file for complete search history.

(56) References Cited

U.S. PATENT DOCUMENTS

| | | | |
|---|---|---|---|
| 2012/0183187 A1 | 7/2012 | Sasaki et al. | |
| 2016/0071264 A1* | 3/2016 | Agam | G06T 11/60 382/128 |
| 2017/0069081 A1* | 3/2017 | Gluncic | G16H 30/40 |
| 2020/0005472 A1 | 1/2020 | Terunuma et al. | |
| 2021/0015440 A1 | 1/2021 | Hamauzu | |

FOREIGN PATENT DOCUMENTS

| | | |
|---|---|---|
| JP | 2017-185007 A | 10/2017 |
| JP | 2018-068863 A | 5/2018 |
| JP | 2019-136323 A | 8/2019 |
| JP | 2021-013685 A | 2/2021 |
| WO | 2017/141498 A1 | 8/2017 |
| WO | 2018/159775 A1 | 9/2018 |

OTHER PUBLICATIONS

An Office Action; "Notice of Reasons for Refusal," mailed by the Japanese Patent Office dated Jan. 10, 2023, which corresponds to Japanese Patent Application No. 2020-180637 and is related to U.S. Appl. No. 17/157,023; with English language translation.

An Office Action; "Decision of Refusal," mailed by the Japanese Patent Office dated May 30, 2023, which corresponds to. Japanese Patent Application No. 2020-180637 and is related to U.S. Appl. No. 17/157,023; with English.

* cited by examiner

RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-022641 filed on Feb. 13, 2020 and Japanese Patent Application No. 2020-180637 filed on Oct. 28, 2020. The above application is hereby expressly incorporated by reference, in its entirety, into the present application.

BACKGROUND

Technical Field

The present disclosure relates to a radiographic image processing device, a radiographic image processing method, and a radiographic image processing program.

Related Art

Various surgical tools, such as gauze to suppress bleeding, a thread and a suture needle for sewing up a wound or an incision, a scalpel and scissors for incision, a drain for draining blood, and forceps for opening an incision, are used in a case in which a surgical operation is performed for a patient. The surgical tools may cause serious complications in a case in which they remain in the body of the patient after surgery. Therefore, it is necessary to check that no surgical tools remain in the body of the patient after surgery.

Therefore, a method has been proposed which prepares a trained model that has learned the characteristics of a gauze image and inputs an image acquired by capturing a surgical field with a camera to a discriminator to discriminate whether or not gauze is present (see JP2018-068863A).

However, a radiographic image in which a surgical tool, such as gauze necessary for training the trained model, remains is extremely rare. For this reason, even though the radiographic image acquired by capturing an image of the subject undergone surgery is input to the discriminator, the surgical tool is not detected in many cases. As such, in a case in which the surgical tool continues not to be detected from the radiographic image, the operator does not know whether or not the discriminator is functioning correctly.

SUMMARY OF THE INVENTION

The present disclosure has been made in view of the above-mentioned problems, and an object of the present disclosure is to enable an operator to check whether or not a discriminator for detecting a surgical tool from a radiographic image is functioning correctly.

According to an aspect of the present disclosure, there is provided a radiographic image processing device comprising at least one processor. The processor acquires a confirmation radiographic image including a surgical tool and detects a region of the surgical tool from the confirmation radiographic image using a trained model that detects the region of the surgical tool included in a radiographic image.

In addition, in the radiographic image processing device according to the aspect of the present disclosure, the processor may output a detection result.

Further, in the radiographic image processing device according to the aspect of the present disclosure, the processor may combine a radiographic image including a human body and a surgical tool image indicating the surgical tool to acquire the confirmation radiographic image.

Furthermore, in the radiographic image processing device according to the aspect of the present disclosure, the surgical tool image may be acquired by performing radiography on the surgical tool.

Moreover, in the radiographic image processing device according to the aspect of the present disclosure, the radiographic image including the human body may be acquired by capturing an image of the human body with an imaging apparatus in a facility having the radiographic image processing device.

In addition, in the radiographic image processing device according to the aspect of the present disclosure, the surgical tool image may be acquired by capturing an image of the surgical tool used in the facility having the radiographic image processing device with the imaging apparatus in the facility.

Further, in the radiographic image processing device according to the aspect of the present disclosure, the surgical tool image may be acquired by a method other than radiography.

Furthermore, in the radiographic image processing device according to the aspect of the present disclosure, the processor may combine the radiographic image and the surgical tool image with combination parameters corresponding to characteristics of at least one of the radiographic image or the surgical tool to generate the confirmation radiographic image.

Moreover, in the radiographic image processing device according to the aspect of the present disclosure, the processor may set the combination parameters according to at least one of radiation absorptivity of the surgical tool, a degree of scattering of radiation in the radiographic image, beam hardening in the radiographic image, or noise corresponding to imaging conditions of the radiographic image.

In addition, in the radiographic image processing device according to the aspect of the present disclosure, the surgical tool may include at least one of gauze, a scalpel, scissors, a drain, a suture needle, a thread, forceps, or a stent graft.

In this case, at least a portion of the gauze may include a radiation absorbing thread.

Further, in the radiographic image processing device according to the aspect of the present disclosure, information indicating that the confirmation radiographic image is for confirmation may be superimposed on the confirmation radiographic image.

According to another aspect of the present disclosure, there is provided a radiographic image processing method comprising: acquiring a confirmation radiographic image including a surgical tool; and detecting a region of the surgical tool from the confirmation radiographic image using a trained model that detects the region of the surgical tool included in a radiographic image.

In addition, a program that causes a computer to perform the radiographic image processing method according to the aspect of the present disclosure may be provided.

According to the aspects of the present disclosure, the operator can check whether or not a trained model for detecting a surgical tool from a radiographic image is functioning correctly.

DETAILED DESCRIPTION

Figure 1:
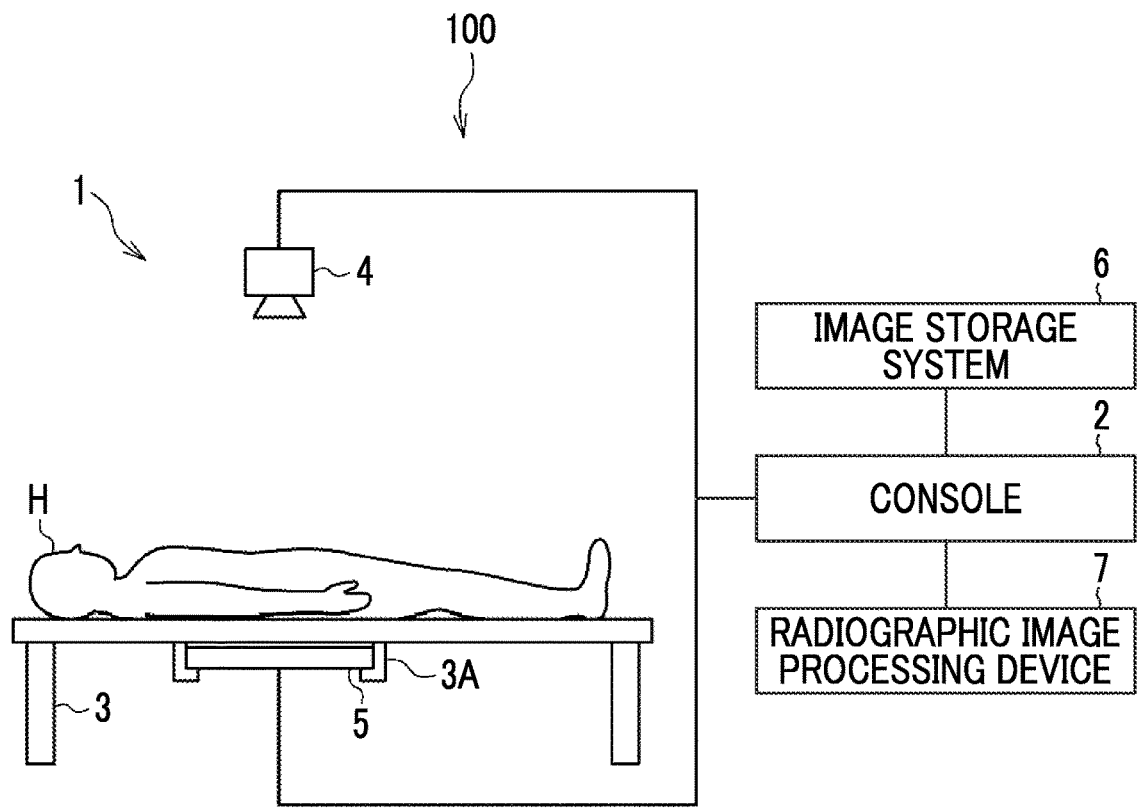
FIG. 1 is a block diagram schematically illustrating a configuration of a radiography system to which a radiographic image processing device according to an embodiment of the present disclosure is applied.

Hereinafter, embodiments of the present disclosure will be described with reference to the drawings. FIG. 1 is a block diagram schematically illustrating a configuration of a radiography system to which a radiographic image processing device according to an embodiment of the present disclosure is applied. As illustrated in FIG. 1, a radiography system 100 according to this embodiment acquires a radiographic image of a subject that is a patient undergone a surgical operation and detects a surgical tool included in the radiographic image. The radiography system 100 according to this embodiment comprises an imaging apparatus 1, a console 2, an image storage system 6, and a radiographic image processing device 7. In addition, the imaging apparatus 1, the console 2, and the radiographic image processing device 7 are installed in the same facility (for example, a hospital and a clinic).

The imaging apparatus 1 detects radiation, which has been emitted from a radiation source 4, such as an X-ray source, and transmitted through a subject H, with a radiation detector 5 to acquire a radiographic image G0 of the subject H that lies supine on an operating table 3. The radiographic image G0 is input to the console 2.

The radiation detector 5 is a portable radiation detector and is attached to the operating table 3 by an attachment portion 3A that is provided in the operating table 3. In addition, the radiation detector 5 may be fixed to the operating table 3.

The console 2 has a function of controlling the imaging apparatus 1 using, for example, an imaging order and various kinds of information acquired from a radiology information system (RIS) (not illustrated) or the like through a network, such as a wireless communication local area network (LAN), and commands or the like directly issued by an engineer or the like. For example, in this embodiment, a server computer is used as the console 2.

The image storage system 6 is a system that stores image data of the radiographic images captured by the imaging apparatus 1. The image storage system 6 extracts an image corresponding to a request from, for example, the console 2 and the radiographic image processing device 7 from the stored radiographic images and transmits the image to a device that is the source of the request. A specific example of the image storage system 6 is a picture archiving and communication system (PACS).

Figure 2:
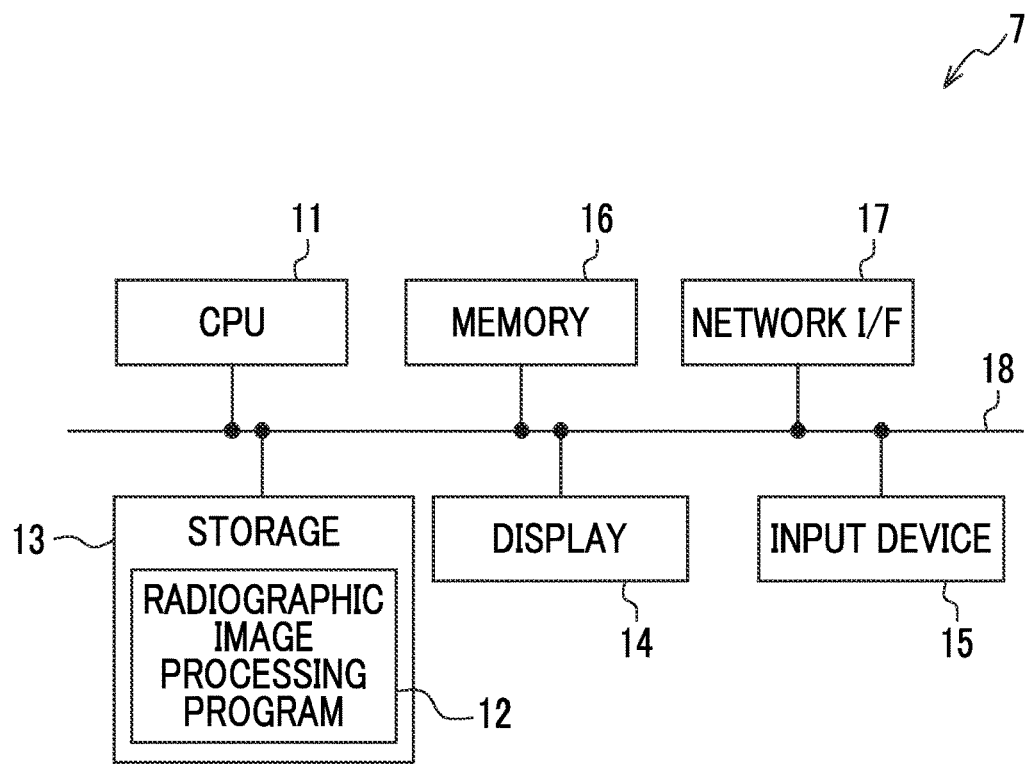
FIG. 2 is a diagram schematically illustrating a configuration of the radiographic image processing device according to this embodiment.

Next, the radiographic image processing device according to this embodiment will be described. First, the hardware configuration of the radiographic image processing device according to this embodiment will be described with reference to FIG. 2. As illustrated in FIG. 2, the radiographic image processing device 7 is a computer, such as a workstation, a server computer, or a personal computer, and comprises a central processing unit (CPU) 11, a non-volatile storage 13, and a memory 16 as a temporary storage area. In addition, the radiographic image processing device 7 comprises a display 14, such as a liquid crystal display, an input device 15, such as a keyboard and a mouse, and a network interface (I/F) 17 that is connected to a network 10. The CPU 11, the storage 13, the display 14, the input device 15, the memory 16, and the network OF 17 are connected to a bus 18. The CPU 11 is an example of a processor according to the present disclosure.

The storage 13 is implemented by, for example, a hard disk drive (HDD), a solid state drive (SSD), and a flash memory. A radiographic image processing program 12 installed in the radiographic image processing device 7 is stored in the storage 13 as a storage medium. The CPU 11 reads the radiographic image processing program 12 from the storage 13, expands the radiographic image processing program 12 in the memory 16, and executes the expanded radiographic image processing program 12.

In addition, the radiographic image processing program 12 is stored in a storage device of the server computer connected to the network or a network storage so as to be accessed from the outside and is downloaded and installed in the computer forming the radiographic image processing device 7 on demand Alternatively, the programs are recorded on a recording medium, such as a digital versatile disc (DVD) or a compact disc read only memory (CD-ROM), are distributed and installed in the computer forming the radiographic image processing device 7 from the recording medium.

Figure 3:
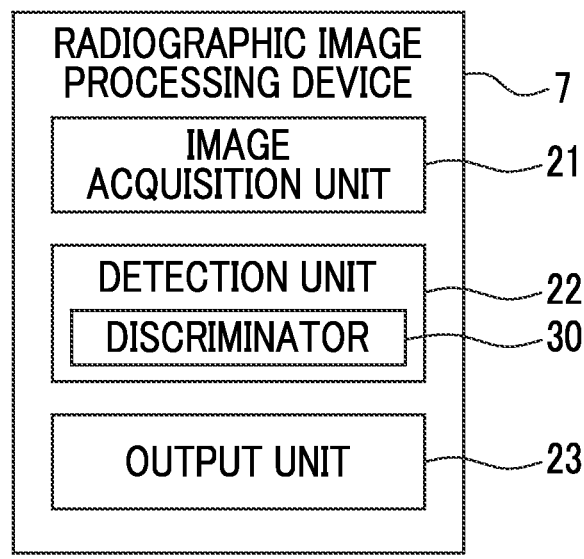
FIG. 3 is a diagram illustrating the functional configuration of the radiographic image processing device according to this embodiment.

Next, the functional configuration of the radiographic image processing device according to this embodiment will be described. FIG. 3 is a diagram schematically illustrating the functional configuration of the radiographic image processing device according to this embodiment. As illustrated in FIG. 3, the radiographic image processing device 7 comprises an image acquisition unit 21, a detection unit 22, and an output unit 23. Then, the CPU 11 executes the radiographic image processing program 12 to function as the image acquisition unit 21, the detection unit 22, and the output unit 23.

The image acquisition unit 21 acquires a radiographic image captured by the imaging apparatus 1 under the control of the console 2. The image acquisition unit 21 acquires a radiographic image from the console 2 or the image storage system 6 through the network I/F 17. Further, the console 2 drives the radiation source 4 to irradiate the subject H that has undergone surgery with radiation and detects the radiation transmitted through the subject H using the radiation detector 5 to acquire a radiographic image G1 from which the surgical tool is to be detected. In this case, the console 2 sets imaging conditions, such as the type of target and filter used in the radiation source 4, an imaging dose, a tube voltage, and a source image receptor distance (SID).

Figure 4:
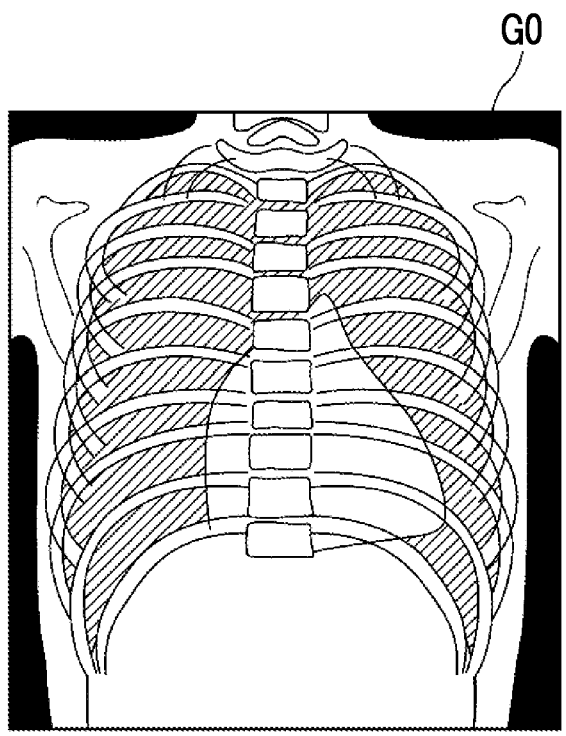
FIG. 4 is a diagram illustrating a radiographic image for generating a confirmation radiographic image.

In addition, the image acquisition unit 21 acquires a confirmation radiographic image T0 including the surgical tool. In this embodiment, the image acquisition unit 21 generates and acquires the confirmation radiographic image T0. Therefore, the image acquisition unit 21 acquires the radiographic image G0 including any subject H for generating the confirmation radiographic image T0 from the image storage system 6 through the network I/F 17. FIG. 4 is a diagram illustrating the radiographic image G0. In addition, FIG. 4 illustrates the radiographic image of the chest of the human body. However, the subject included in the radiographic image G0 is not limited thereto. Further, the radiographic image G0 for generating the confirmation radiographic image T0 is acquired by the imaging apparatus 1 that is installed in the same facility as the radiographic image processing device 7 according to this embodiment and is then stored in the image storage system 6.

Figure 5:
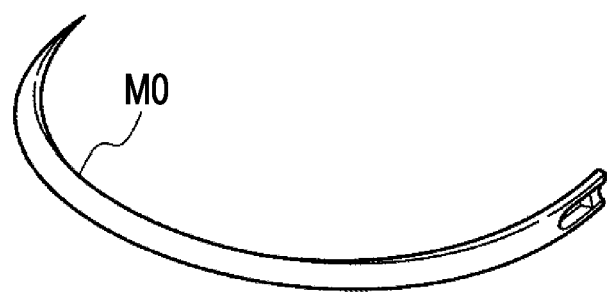
FIG. 5 is a diagram illustrating an image of a suture needle as a surgical tool.

In addition, the image acquisition unit 21 acquires a surgical tool image M0 indicating a surgical tool from the image storage system 6 in order to generate the confirmation radiographic image T0. In this embodiment, the surgical tool image M0 is an image that is acquired by a method other than radiography. For example, the surgical tool image M0 is a three-dimensional image indicating a surgical tool which has been created by computer graphics or the like. In addition, in this embodiment, it is assumed that a suture needle for sewing up a wound or an incision is used as the surgical tool. FIG. 5 is a diagram illustrating the image of the suture needle as the surgical tool. In FIG. 5, the surgical tool image M0 of the suture needle is two-dimensionally illustrated. However, it is assumed that the surgical tool image M0 can be three-dimensionally rotated or moved. In addition, the surgical tool image M0 may be a photographic image of the surgical tool. In a case in which the surgical tool image M0 is a photographic image, it is preferable to acquire the surgical tool image M0 by capturing a photograph of the surgical tool used in the facility in which the radiographic image processing device 7 according to this embodiment is installed.

In addition, the image acquisition unit 21 combines the surgical tool image M0 with the radiographic image G0 to generate the confirmation radiographic image T0. The image acquisition unit 21 combines the radiographic image G0 and the surgical tool image M0 with combination parameters corresponding to the characteristics of at least one of the radiographic image G0 or the surgical tool (the suture needle in this embodiment) to generate the confirmation radiographic image T0. The image acquisition unit 21 sets the combination parameters according to at least one of the radiation absorptivity of the surgical tool (the suture needle in this embodiment), the degree of scattering of radiation by the surgical tool, beam hardening in the radiographic image G0, or noise corresponding to the imaging conditions of the radiographic image G0.

In addition, the radiographic image G0 may be displayed on the display 14, and the position of the surgical tool image M0 and the orientation of the surgical tool image M0 in the radiographic image G0 may be designated by a command input by the operator through the input device 15.

Figure 6:
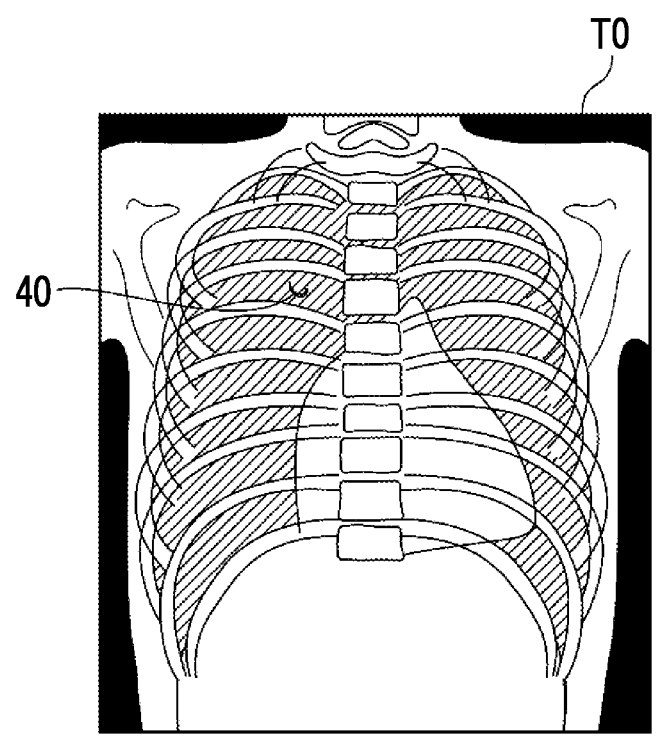
FIG. 6 is a diagram illustrating the confirmation radiographic image.

In this embodiment, for example, it is assumed that the image acquisition unit 21 generates the confirmation radiographic image T0 using the following Expression (1). That is, in pixels (x, y) of a region of the radiographic image G0 which is combined with the surgical tool image M0, the image acquisition unit 21 subtracts a pixel value M0(x, y) of the surgical tool image M0 weighted by a weight coefficient w1 from a pixel value G0(x, y) of the radiographic image G0 to derive a pixel value T0(x, y) of the confirmation radiographic image T0. In addition, the weight coefficient w1 has a value that is equal to or greater than 0 and equal to or less than 1. The weight coefficient w1 is included in the combination parameters according to this embodiment. FIG. 6 is a diagram illustrating the confirmation radiographic image. As illustrated in FIG. 6, in the confirmation radiographic image T0, a suture needle 40 is included in the right lung of the subject.

$$T0(x, y) = G0(x, y) - w1 \cdot M0(x, y) \quad (1)$$

Here, in a case in which the radiation absorptivity of the surgical tool is high, the contrast of the surgical tool is high in the radiographic image acquired by performing radiography on the surgical tool. For example, in a case in which the surgical tool is a metal tool, such as a suture needle, scissors, or a scalpel, the contrast of the radiographic image of the surgical tool is high. Therefore, in a case in which weighted subtraction between the radiographic image G0 and the surgical tool image M0 is performed, the image acquisition unit 21 increases the weight coefficient w1 for the surgical tool image M0 such that the contrast of the surgical tool is not too high in the confirmation radiographic image T0.

Further, the contrast of the radiographic image G0 is reduced due to the scattering of radiation. The influence of the scattering of radiation becomes larger as the body thickness of the subject H becomes larger. In addition, as the body thickness of the subject H becomes larger, the density of a subject region included in the radiographic image G0 becomes lower. Therefore, the image acquisition unit 21 derives the average value of the density of the subject region included in the radiographic image G0, reduces the weight coefficient w1 such that a difference in density between the radiographic image G0 and the surgical tool image M0 becomes smaller as the average value becomes smaller, that is, the body thickness of the subject H becomes larger, and generates the confirmation radiographic image T0.

Here, beam hardening occurs in which, as the tube voltage applied to the radiation source 4 becomes higher and the energy of radiation becomes higher, a lower-energy component of the radiation is absorbed by the subject H and the energy of the radiation becomes higher while the radiation is transmitted through the subject H. In a case in which the beam hardening occurs, the contrast of the radiographic image decreases. Further, the increase in the energy of radiation due to the beam hardening becomes more significant as the body thickness of the subject H becomes larger. In addition, as the body thickness of the subject H becomes larger, the density of the subject region included in the radiographic image G0 becomes lower. Therefore, the image acquisition unit 21 derives the average value of the density of the subject region included in the radiographic image G0, reduces the weight coefficient w1 such that a difference in density between the radiographic image G0 and the surgical tool image M0 becomes smaller as the average value becomes smaller, that is, the body thickness of the subject H becomes larger, and generates the confirmation radiographic image T0.

In addition, in a case in which the radiation dose in the imaging conditions is reduced, the amount of noise included in the radiographic image G0 increases. Therefore, in a case in which the radiation dose is small, the image acquisition unit 21 adds noise N(x, y) corresponding to the radiation dose to Expression (1) to generate the confirmation radiographic image T0, as represented by the following Expression (2). In this case, the weight coefficient w1 may be a predetermined value or may be set according to at least one of the radiation absorptivity of the surgical tool, the degree of scattering of radiation, or the beam hardening. Further, the noise N(x, y) may be derived by a predetermined simulation and may be stored in the storage 13. In addition, the noise N(x, y) is included in the combination parameters.

$$T0(x, y)=G0(x, y)-w1 \cdot M0(x, y)+N(x, y) \qquad (2)$$

In this embodiment, the image acquisition unit 21 may change the combination position of the surgical tool image M0 in the radiographic image G0 or the combination parameters to generate a plurality of confirmation radiographic images T0. Therefore, the confirmation radiographic image T0 obtained by combining the surgical tool image M0 with the radiographic image G0 as if the surgical tool image M0 is acquired by radiography is generated. In addition, the confirmation radiographic image T0 may be generated using a plurality of radiographic images G0 having different subjects H.

In addition, the surgical tool image M0 may be acquired by performing radiography on the surgical tool. In this case, it is preferable that the surgical tool image M0 is acquired by capturing the image of the surgical tool used in the facility, in which the radiographic image processing device 7 according to this embodiment is installed, using the imaging apparatus 1 installed in the facility. Even in this case, the confirmation radiographic image T0 may be generated by combining the surgical tool image M0 with the radiographic image G0 while appropriately setting the combination parameters.

The detection unit 22 detects a region of the surgical tool in the radiographic image G1 as a detection target. For the detection, a discriminator 30 that has been subjected to machine learning so as to detect the region of the surgical tool included in the radiographic image G1 in a case in which the radiographic image G1 as the detection target is input is applied to the detection unit 22. In addition, the discriminator 30 is an example of a trained model. Therefore, in a case in which the radiographic image G1 as the detection target is input to the detection unit 22, the detection unit 22 directs the discriminator 30 to discriminate the region of the surgical tool included in the radiographic image G1 as the detection target, thereby detecting the region of the surgical tool.

Here, the discriminator 30 is constructed by training a machine learning model using the radiographic image including the surgical tool as training data. In this embodiment, a suture needle is used as the surgical tool, and the discriminator 30 is trained so as to detect the suture needle as the surgical tool in a case in which a radiographic image is input.

In addition, A machine learning model can be used as the discriminator 30. One example of the machine learning model is a neural network model. Examples of the neural network model include a simple perceptron, a multilayer perceptron, a deep neural network, a convolutional neural network, a deep belief network, a recurrent neural network, and a stochastic neural network.

Figure 7:
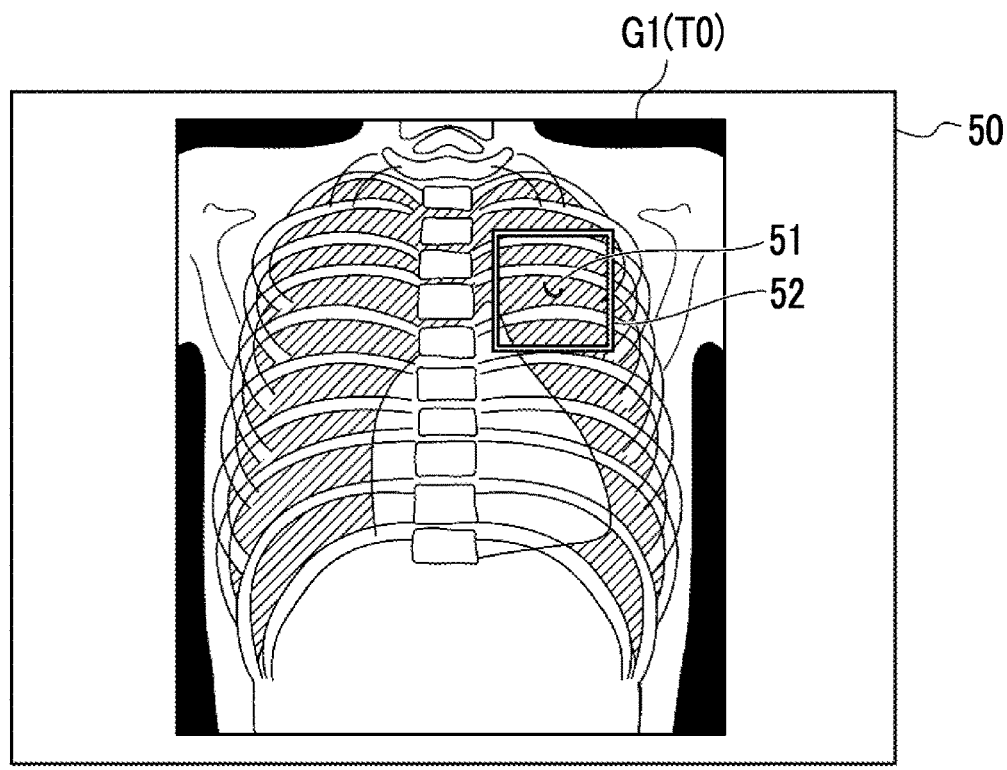
FIG. 7 is a diagram illustrating a radiographic image display screen in a case in which the surgical tool has been detected.

The output unit 23 displays the radiographic image G1 or the confirmation radiographic image T0 on the display 14 such that the region of the surgical tool detected from the radiographic image G1 or the confirmation radiographic image T0 as the detection target by the detection unit 22 as described below is highlighted. FIG. 7 is a diagram illustrating a radiographic image display screen in a case in which a surgical tool is detected. As illustrated in FIG. 7, the radiographic image G1 or the confirmation radiographic image T0 as the detection target is displayed on a display screen 50, and a surgical tool region 51 included in the radiographic image G1 or the confirmation radiographic image T0 is surrounded by a rectangular region 52 so as to be highlighted. In addition, the rectangular region 52 is illustrated in white in FIG. 7. However, the rectangular region 52 may be colored. Further, instead of giving the rectangular region 52, a mark, such as an arrow or an asterisk, may be given in the vicinity of the surgical tool region to highlight the surgical tool region.

Furthermore, in a case in which the radiographic image G1 or the confirmation radiographic image T0 is displayed on the display 14, image processing for display, such as a gradation conversion process or a density conversion process, may be performed on the radiographic image G1 or the confirmation radiographic image T0 in order for the operator to easily observe the displayed radiographic image G1 or confirmation radiographic image T0. The output unit 23 may perform the image processing for display, or an image processing unit for performing the image processing for display may be separately provided. In addition, in a case in which the image processing for display is performed on the radiographic image G1 or the confirmation radiographic image T0, the detection unit 22 may detect the region of the surgical tool from the radiographic image G1 or the confirmation radiographic image T0 subjected to the image processing for display.

Figure 8:
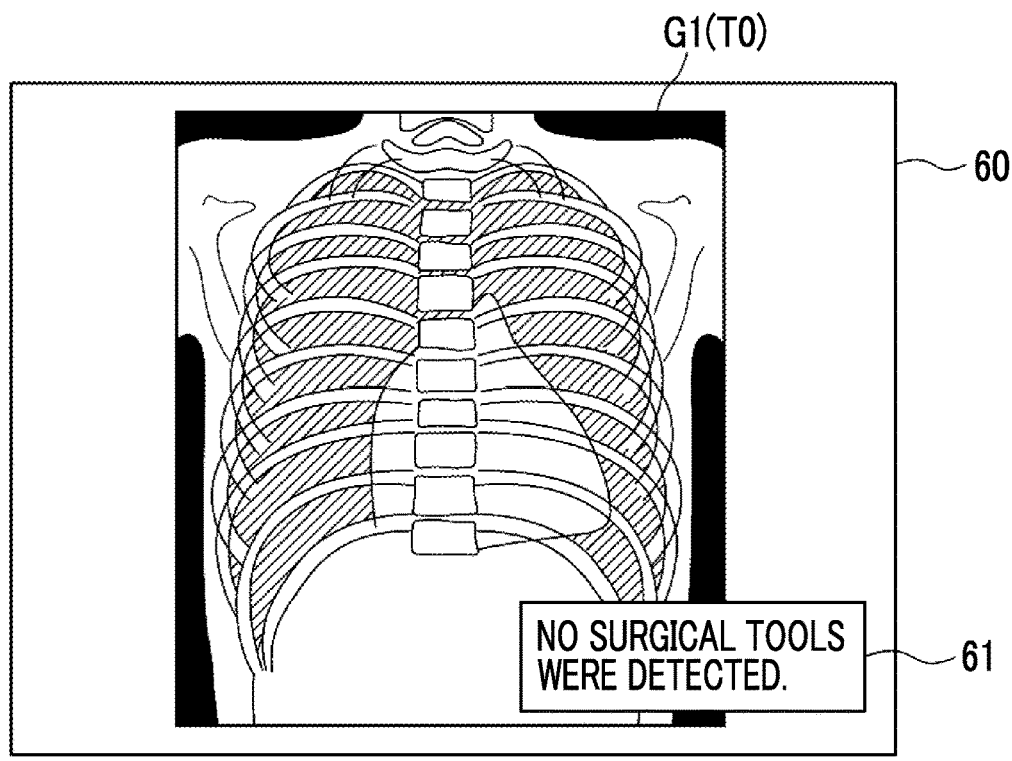
FIG. 8 is a diagram illustrating a notification screen in a case in which a region of the surgical tool has not been detected.

Further, in a case in which the detection unit 22 does not detect the region of the surgical tool from the radiographic image G1 or the confirmation radiographic image T0, the output unit 23 notifies the fact. FIG. 8 is a diagram illustrating a notification screen in a case in which no surgical tools have been detected. As illustrated in FIG. 8, a message 61 of "No surgical tools were detected." is displayed on a notification screen 60 so as to be superimposed on the radiographic image G1 or the confirmation radiographic image T0. In addition, instead of the message 61, for example, an icon or a mark indicating that no surgical tools have been detected may be displayed. Further, the turn-on and turn-off of the display of the message 61 may be switched by a command from the input device 15.

Here, the radiographic image in which the surgical tool necessary for training the discriminator 30 included in the detection unit 22 remains is extremely rare. Therefore, even though the radiographic image G1 as the detection target, which has been acquired by capturing the image of the subject H undergone surgery, is input to the discriminator 30, the surgical tool is not detected in many cases. As such, in a case in which the surgical tool continues not to be detected from the radiographic image G1, the operator does not know whether or not the discriminator 30 is functioning correctly. Therefore, in this embodiment, the detection unit 22 is directed to detect the region of the surgical tool from the confirmation radiographic image T0 including the surgical tool such that the operator can check whether or not the discriminator 30 of the detection unit 22 is functioning correctly.

Figure 9:
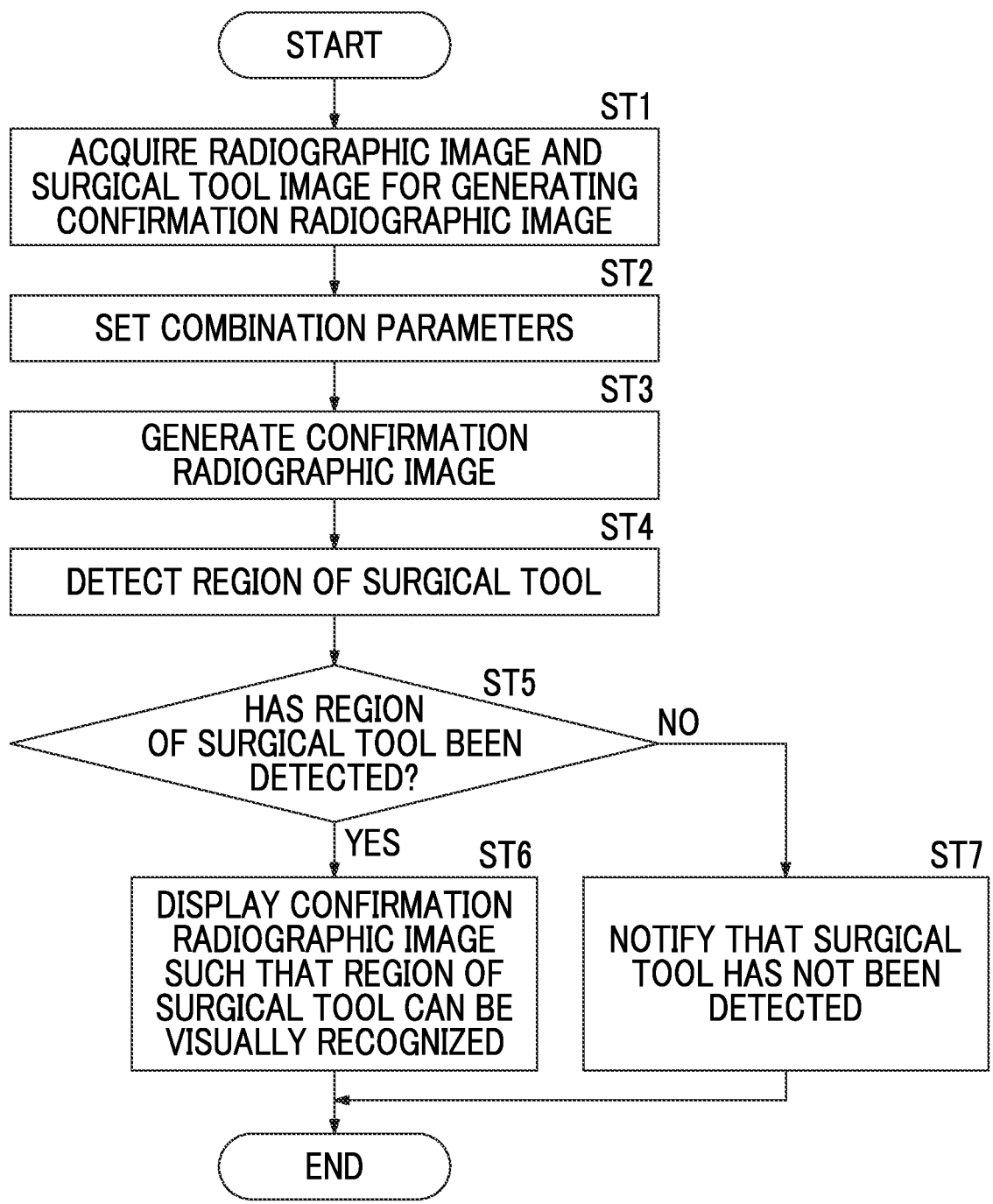
FIG. 9 is a flowchart illustrating a process performed in this embodiment.

Next, a process performed in this embodiment using the confirmation radiographic image T0 will be described. FIG. 9 is a flowchart illustrating the process performed in this embodiment. First, the image acquisition unit 21 acquires the radiographic image G0 and the surgical tool image M0 for generating the confirmation radiographic image T0 (Step ST1). Then, the image acquisition unit 21 sets combination parameters for the radiographic image G0 and the surgical tool image M0 (Step ST2) and combines the radiographic image G0 and the surgical tool image M0 according to the combination parameters to generate the confirmation radiographic image T0 (Step ST3).

Then, the detection unit 22 detects the region of the surgical tool from the confirmation radiographic image T0 (Step ST4). In a case in which the region of the surgical tool has been detected from the confirmation radiographic image T0 (Step ST5: YES), the output unit 23 displays the confirmation radiographic image T0 on the display 14 such that the region of the surgical tool can be visually recognized (Step ST6). Then, the processing ends. On the other hand, in a case in which the region of the surgical tool has not been detected in Step ST5, the output unit 23 notifies that the region of the surgical tool has not been detected (notification that no surgical tools have been detected; Step ST7). Then, the process ends.

As such, in this embodiment, the confirmation radiographic image T0 including the surgical tool is acquired, and the detection unit 22 detects the surgical tool from the confirmation radiographic image T0. The confirmation radiographic image T0 includes the surgical tool. Therefore, in a case in which the surgical tool is detected from the confirmation radiographic image T0, the display screen 50 illustrated in FIG. 7 is displayed on the display 14. Therefore, the display of the display screen 50 makes it possible for the operator to check that the discriminator 30 of the detection unit 22 is functioning correctly. On the other hand, in a case in which the surgical tool is not detected from the confirmation radiographic image T0, the notification screen 60 illustrated in FIG. 8 is displayed on the display 14. In this case, the display of the notification screen 60 makes it possible for the operator to check that the discriminator 30 of the detection unit 22 is not functioning correctly. Therefore, according to this embodiment, the operator can check whether or not the discriminator 30 is functioning correctly.

In the above-described embodiment, the suture needle as the surgical tool is the detection target. However, the present disclosure is not limited thereto. Any surgical tools used in surgery, such as gauze, a scalpel, scissors, a drain, a thread, forceps, or a stent graft, can be used as the detection target. In this case, the discriminator 30 may be trained so as to discriminate the target surgical tool. In addition, the discriminator 30 may be constructed such that it is trained to detect a plurality of channels and discriminates not only one kind of surgical tool but also a plurality of kinds of surgical tools.

Figure 10:
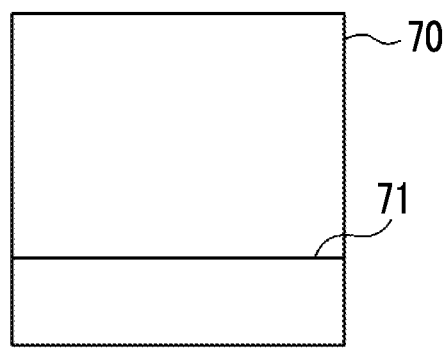
FIG. 10 is a diagram illustrating gauze.
Figure 11:
FIG. 11 is a diagram illustrating an image of the gauze as the surgical tool.

Here, gauze used as the surgical tool will be described. FIG. 10 is a diagram illustrating gauze. As illustrated in FIG. 10, gauze 70 is a plain-woven cotton fabric and a radiation absorbing thread 71 is woven in a portion of the gauze 70. Cotton yarn transmits radiation and the radiation absorbing thread 71 absorbs radiation. Therefore, the radiographic image of the gauze 70 includes only the linear radiation absorbing thread 71. Here, during surgery, the gauze 70 is rolled and inserted into the human body in order to absorb blood. Therefore, an image indicating a state in which the radiation absorbing thread 71 is rolled is used as the surgical tool image M0 to be combined with the radiographic image G0 in order to generate the confirmation radiographic image T0, as illustrated in FIG. 11.

Further, in the above-described embodiment, the image acquisition unit 21 generates the confirmation radiographic image T0 from the radiographic image G0 and the surgical tool image M0. However, the present invention is not limited thereto. The confirmation radiographic image T0 may be stored in the image storage system 6 and may be acquired from the image storage system 6.

Further, in the above-described embodiment, the output unit 23 displays the display screen 50 illustrated in FIG. 7 in a case in which the region of the surgical tool has been detected from the confirmation radiographic image T0, and displays the notification screen 60 illustrated in FIG. 8 in a case in which the region of the surgical tool has not been detected. However, the present invention is not limited thereto. The output unit 23 may notify the detection result of the region of the surgical tool from the confirmation radiographic image T0 by voice. Furthermore, the display screen 50 illustrated in FIG. 7, the notification screen 60 illustrated in FIG. 8, and the voice may be output together.

Figure 12:
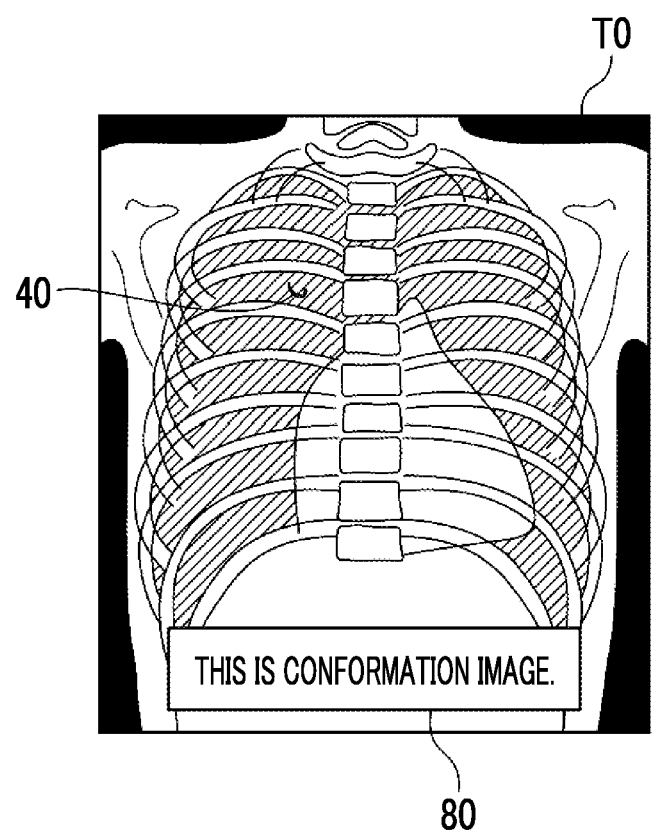
FIG. 12 is a diagram illustrating the confirmation radiographic image on which information indicating that the confirmation radiographic image is for confirmation has been superimposed.

In addition, in the above-described embodiment, information indicating that the confirmation radiographic image T0 is for confirmation may be superposed on the confirmation radiographic image T0. FIG. 12 is a diagram illustrating a confirmation radiographic image on which information indicating that the confirmation radiographic image is for confirmation has been superimposed. As illustrated in FIG. 12, as the information indicating that the confirmation radiographic image T0 is for confirmation, a caption 80 of "This is a confirmation image." is superimposed on the confirmation radiographic image T0. Further, the content of the caption 80 is not limited thereto as long as it indicates that the confirmation radiographic image is for confirmation. For example, other texts, such as "Please do not use for diagnosis", can be used. Furthermore, it is preferable that the caption 80 is incorporated into the confirmation radiographic image T0. In addition, instead of the caption 80, for example, a mark indicating that the confirmation radiographic image T0 is for confirmation may be used. As such, since the information indicating that the confirmation radiographic image T0 is for confirmation is superimposed on the confirmation radiographic image T0, it is possible to prevent the operator from mistaking the confirmation radiographic image T0 for a clinical radiographic image that is actually used for diagnosis and using the confirmation radiographic image T0 for diagnosis.

In addition, in the above-described embodiment, the radiation is not particularly limited. For example, α-rays or γ-rays other than X-rays can be applied.

In the above-described embodiment, for example, the following various processors can be used as a hardware structure of processing units performing various processes, such as the image acquisition unit 21, the detection unit 22, and the output unit 23. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiographic image processing device comprising:
   at least one processor,
   wherein the processor acquires a confirmation radiographic image T0(x, y) including a surgical tool, wherein the confirmation radiographic image T0(x, y) is obtained by combining a radiographic image G0 including a human body and a surgical tool image M0 which indicates the surgical tool by equation (1) using a weight coefficient w1, which is a combination of parameters corresponding to characteristics of at least one of the radiographic image or the surgical tool, wherein the (x, y) is the pixel of the radiographic image G0 where the surgical tool image is combined, and wherein the weight coefficient w1 is set so as to increase as radiation absorptivity of the surgical tool is higher, and is set so as to decrease as an average value of a density of a subject region included in the radiographic image is lower; and
   detects a region of the surgical tool from the confirmation radiographic image using a trained model that detects the region of the surgical tool in a target radiographic image in a case that the region of the surgical tool is included in the target radiographic image:

$$T0(x, y) = G0(x, y) - w1 \cdot M0(x, y) \qquad (1).$$

2. The radiographic image processing device according to claim 1,
   wherein the processor outputs a detection result.

3. The radiographic image processing device according to claim 1,
   wherein the processor combines the radiographic image including the human body and the surgical tool image indicating the surgical tool to acquire the confirmation radiographic image.

4. The radiographic image processing device according to claim 3,
   wherein the surgical tool image is acquired by performing radiography on the surgical tool.

5. The radiographic image processing device according to claim 3,
   wherein the radiographic image including the human body is acquired by capturing an image of the human body with an imaging apparatus in a facility having the radiographic image processing device.

6. The radiographic image processing device according to claim 5,
   wherein the surgical tool image is acquired by capturing an image of the surgical tool used in the facility having the radiographic image processing device with the imaging apparatus in the facility.

7. The radiographic image processing device according to claim 3,
   wherein the surgical tool image is acquired by a method other than radiography.

8. The radiographic image processing device according to claim 3,
   wherein the processor combines the radiographic image and the surgical tool image with the combination parameters corresponding to characteristics of at least one of the radiographic image or the surgical tool to generate the confirmation radiographic image.

9. The radiographic image processing device according to claim 8,
   wherein the processor sets the combination parameters according to at least one of radiation absorptivity of the surgical tool, a degree of scattering of radiation in the radiographic image, beam hardening in the radiographic image, or noise corresponding to imaging conditions of the radiographic image.

10. The radiographic image processing device according to claim 1,
    wherein the surgical tool consists of at least one of gauze, a scalpel, scissors, a drain, a suture needle, a thread, forceps, or a stent graft.

11. The radiographic image processing device according to claim 10,
    wherein at least a portion of the gauze includes a radiation absorbing thread.

12. The radiographic image processing device according to claim 1,
    wherein information indicating that the confirmation radiographic image is for confirmation is superimposed on the confirmation radiographic image.

13. A radiographic image processing method comprising:
    acquiring a confirmation radiographic image T0(x, y) including a surgical tool, wherein the confirmation radiographic image T0(x, y) is obtained by combining a radiographic image G0 including a human body and a surgical tool image M0 which indicates the surgical tool by equation (1) using a weight coefficient w1, which is a combination of parameters corresponding to characteristics of at least one of the radiographic image or the surgical tool, wherein the (x, y) is the pixel of the radiographic image G0 where the surgical tool image is combined, and wherein the weight coefficient w1 is set so as to increase as radiation absorptivity of the surgical tool is higher, and is set so as to decrease as an average value of a density of a subject region included in the radiographic image is lower; and
    detecting a region of the surgical tool from the confirmation radiographic image using a trained model that detects the region of the surgical tool in a target radiographic image in a case that the region of the surgical tool is included in the target radiographic image:

$$T0(x, y) = G0(x, y) - w1 \cdot M0(x, y) \qquad (1).$$

14. A non-transitory computer-readable storage medium that stores a radiographic image processing program that causes a computer to perform:
    a procedure of acquiring a confirmation radiographic image T0(x, y) including a surgical tool, wherein the confirmation radiographic image T0(x, y) is obtained by combining a radiographic image G0 including a human body and a surgical tool image M0 which indicates the surgical tool by equation (1) using a weight coefficient w1, which is a combination of parameters corresponding to characteristics of at least one of the radiographic image or the surgical tool, wherein the (x, y) is the pixel of the radiographic image G0 where the surgical tool image is combined, and wherein the weight coefficient w1 is set so as to increase as radiation absorptivity of the surgical tool is higher, and is set so as to decrease as an average value of a density of a subject region included in the radiographic image is lower; and a procedure of detecting a region of the surgical tool from the confirmation radiographic image using a trained model that detects the region of the surgical tool in a target radiographic image in a case that the region of the surgical tool is included in the target radiographic image:

$$T0(x, y) = G0(x, y) - w1 \cdot M0(x, y) \qquad (1).$$

* * * * *